United States Patent [19]
Robinett

[11] Patent Number: 5,850,043
[45] Date of Patent: Dec. 15, 1998

[54] IN-PLACE SHEAR WALL TESTING METHOD AND APPARATUS

[76] Inventor: Victor B. Robinett, 236 S. Helberta Ave. #A, Redondo Beach, Calif. 90277

[21] Appl. No.: 269,140

[22] Filed: Jun. 30, 1994

[51] Int. Cl.$^6$ .............................. G01M 5/00; G01N 3/20
[52] U.S. Cl. ................................................ 73/786; 73/849
[58] Field of Search ............................ 73/789, 786, 849, 73/825, 837, 788, 819

[56] References Cited

U.S. PATENT DOCUMENTS

| | | | |
|---|---|---|---|
| 3,871,213 | 3/1975 | Jureit et al. ............................... | 73/825 |
| 5,051,919 | 9/1991 | Deuar ......................................... | 73/786 |
| 5,067,353 | 11/1991 | Sersen ....................................... | 73/849 |
| 5,086,651 | 2/1992 | Westermo et al. ........................ | 73/786 |

Primary Examiner—Max H. Noori
Attorney, Agent, or Firm—Edgar W. Averill, Jr.

[57] ABSTRACT

A method and apparatus for the in-place testing of the shear strength of a rectangular area of a wall. The method includes affixing a first shoe to an upper corner of a rectangular area of the wall and a second shoe to the lower opposite corner of this rectangular area. A strut is placed between the two shoes and its length is increased or decreased and measurements are made along the vertical, the horizontal and the diagonal as the length of the strut is changed. Preferably this is done with a hydraulic cylinder. The shoes have holes along a vertical side and a horizontal side and several brackets may be affixed at preferred locations to the sole and a stud at the bottom corner and to the plate and a stud at the top corner. A length adjusting strut is affixed between these attached plates and preferably rests on curved surfaces on each shoe.

15 Claims, 5 Drawing Sheets

IN-PLACE SHEAR WALL TESTING METHOD AND APPARATUS

BACKGROUND OF THE INVENTION

The field of the invention is structural testing and the invention relates more particularly to the testing of completed structures which may have been poorly constructed, damaged by an earthquake, high winds or by aging or other destructive elements. Typically, the strength of a wall is determined by engineering calculations based on the manner in which it has been constructed. Unfortunately, this strength can be decreased by factors such as an earthquake, dry rot and the like. The typical engineering charts are unable to ascertain the damage caused by improper construction technique, the seismic or other harmful activity.

Various structural testing methods and apparatus have been used over the years. One such device is shown in U.S. Pat. No. 1,708,333 wherein an instrument is embedded in a concrete beam and used to measure the deformation of the beam. A method of testing the soundness of a wooden pole is shown in U.S. Pat. No. 2,854,847 where the ground line strength of a telephone pole is determined by placing an artificial stress on the pole and measuring its bending at the ground line. A modified roof strain indicator is shown in U.S. Pat. No. 4,070,906 which is used for the roof of a mine. Two roof bolts are placed in the mine roof and a wire is affixed to the measuring gauge to determine any change in distance between the two roof bolts. Lastly a structural movement measuring device is shown in U.S. Pat. No. 4,472,883. It is useful for measuring movement along the crack in a masonry wall.

None of these devices answer the problem of determining the structural integrity of a building which has been damaged by, for instance, an earthquake.

SUMMARY OF THE INVENTION

It is an object of the present invention to provide apparatus for the in-place testing of the shear strength of a wall of a completed structure.

It is another object of the present invention to provide a device for the in-place testing of the shear strength of a rectangular area of a wall.

The present invention is for a method for the in-place testing of the shear strength of a rectangular area of a wall. The wall has vertical studs, an upper plate and a lower sole plate. Two opposing corners of a rectangular area are exposed and an upper shoe is affixed to the upper corner and a lower shoe is affixed to the lower corner. A force applying length altering strut is placed between the two shoes and initial measurements are taken. Then periodically, as the force applying length altering strut is loaded or unloaded with force, further measurements are taken. Measurements are preferably taken periodically at sequential units of stress to determine how this area of the wall reacts to the force of shear exerted by the length altering strut. Preferably the length altering strut is expanded by a hydraulic cylinder assembly during the test and measurements are taken at periodic predetermined pressure values in the hydraulic cylinder assembly.

The apparatus of the present invention is an assembly having a lower shoe which has a right angled member with a lower portion including a plurality of holes and a vertical portion also having a plurality of holes. A plurality of brackets may be affixed at predetermined places along these two members and to the plate and to a vertical stud. This lower shoe also has a curved strut supporting plate and the upper shoe also has a vertical and horizontal piece with holes and brackets which may be affixed at preferred positions. The upper shoe also has a curved strut supporting surface and a length adjusting strut is placed between the two shoes and assembled so that it rests against the curved area of both shoes. Preferably the upper shoe includes a slot through which a threaded upper portion of the length adjusting strut may be inserted and loosely secured by a nut to assist in the assembly of the device.

DESCRIPTION OF THE PREFERRED EMBODIMENTS

Initially, the problem often facing a structural engineer is an existing structure which may or may not have been severely damaged by an earthquake, tornado or by age. While the typical engineering calculation as to the strength of a wall is normally useful, it does not make any reduction for the amount of damage caused by an earthquake. It furthermore does not taken into account surface covering such as plywood which may actually add strength to the wall, but which may not appear with conventional engineering calculations. Thus, it has been proposed that the actual strength of the wall as covered and as possibly damaged, should be determined by placing an area of the wall under shear stress and measuring the actual movement. In this way the effect of wall coverings as well as wall damage may be accurately ascertained. By determining that a properly selected shear wall meets minimal code values of performance, it is likely to assume that the structure is sound.

Walls to be tested are selected on the basis of where critical seismic forces may be expected and the load to be applied to the test wall is based on the wall's original structural design.

Figure 1:
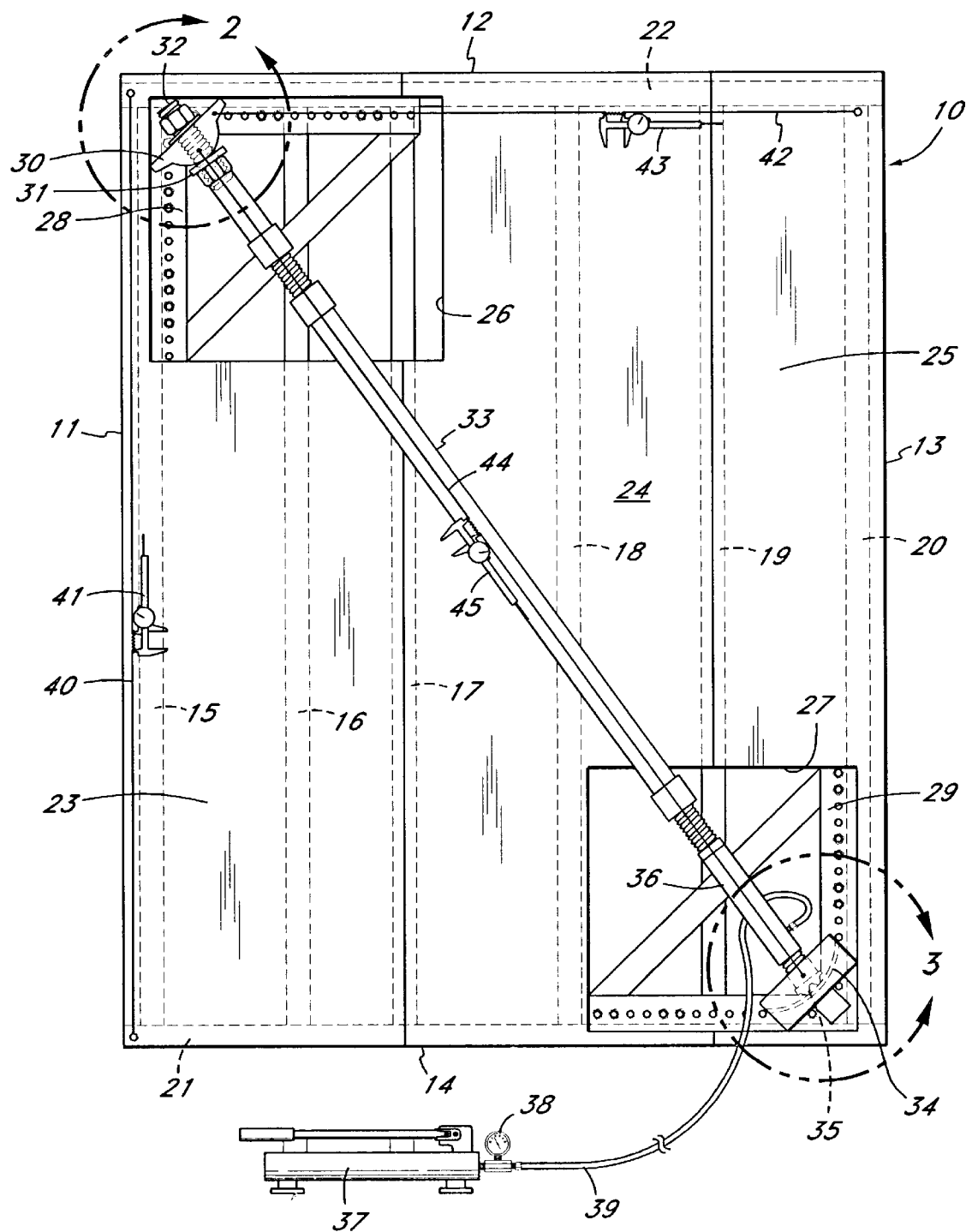
FIG. 1 is a front view of the in-place testing apparatus of the present invention secured to a rectangular area of an existing wall.
Figure 2:
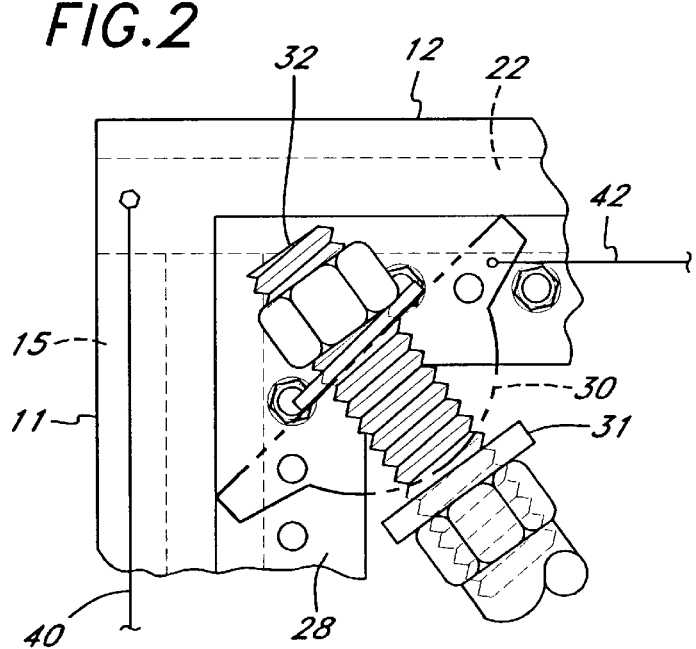
FIG. 2 is an enlarged view taken along line 2—2 of FIG. 1.
Figure 3:
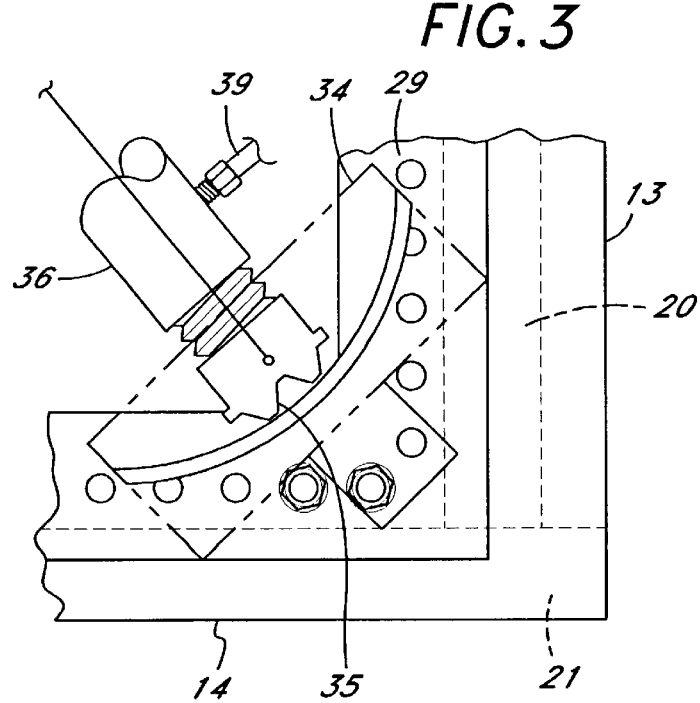
FIG. 3 is an enlarged view taken along line 3—3 of FIG. 1.
Figure 4:
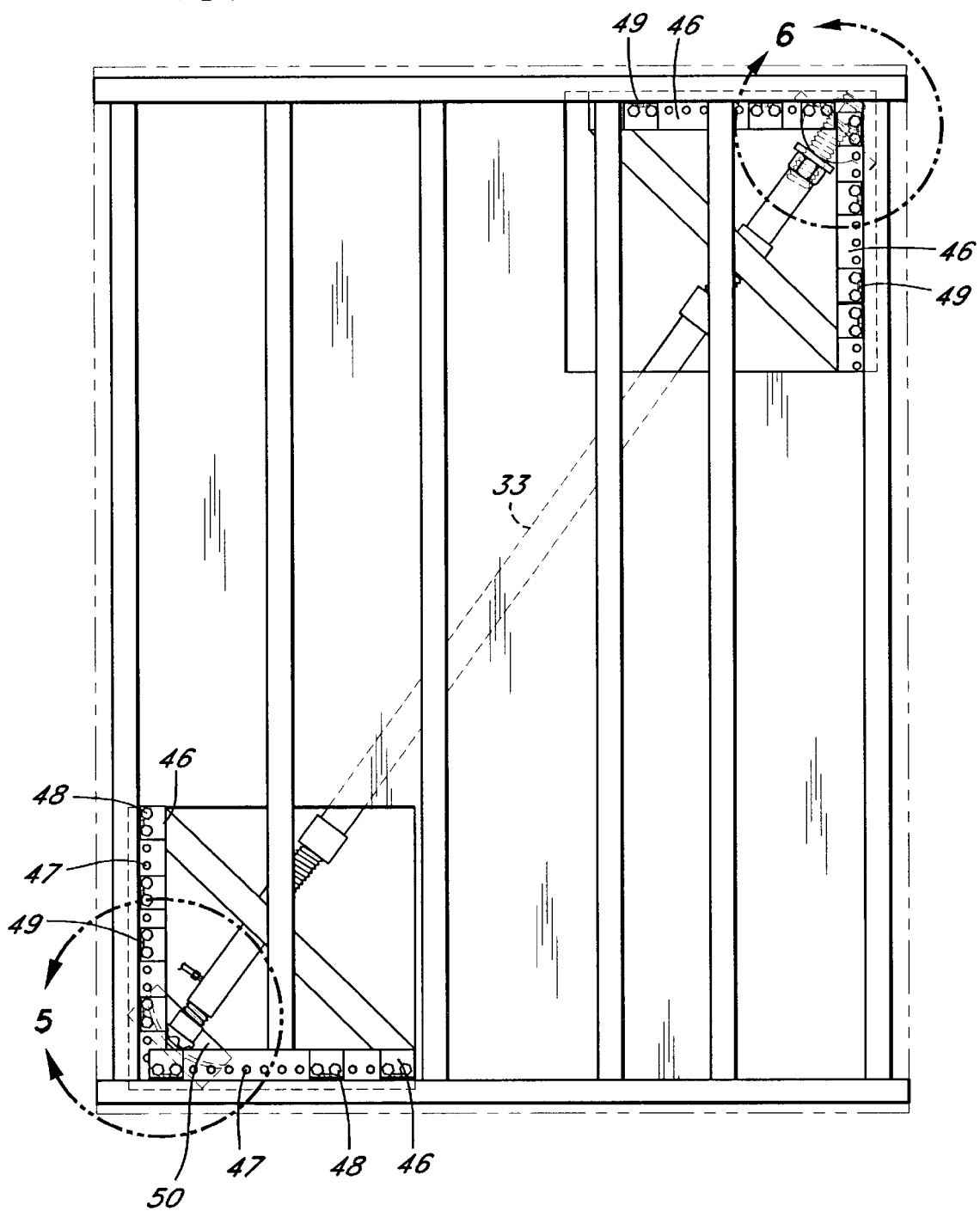
FIG. 4 is a back view of the rectangular wall portion of FIG. 1.

A selected area of a wall 10 is shown in FIG. 1. This area of the wall is a rectangle and has a first side 11, an upper side 12, a second side 13 and a lower side 14. The selected area of wall has vertical studs indicated by reference characters 15, 16, 17, 18, 19 and 20. The studs are held at the base by sole 21 and at the top by plate 22.

The wall has been covered by three pieces of wallboard, 23, 24 and 25. A removed area 26 is made in wallboards 23 and 24 and a lower removed area 27 is made in wallboards 24 and 25. An upper shoe indicated generally by reference character 28 is secured to stud 15 and plate 22. A lower or second shoe 29 is secured to stud 20 and sole 21. The securement method will be discussed in further detail below. The first shoe has a pair of curved strut supporting portions 30 which contacts a plate 31 near the upper end 32 of length altering strut 33. A curved strut supporting portion 34 is held by lower shoe 29 and the lower end 35 of strut 33 contacts curved portion 34. A hydraulic cylinder assembly 36 is placed along length altering strut 33 and a hydraulic pump 37 and gauge 38 pump and measure hydraulic fluid through hose 39 into hydraulic cylinder assembly 36.

Preferably three measuring distances are continuously made. The first one is indicated generally by reference character 40 and is a vertical measuring device which includes a spring loaded caliper 41. The second measuring device 42 measures the horizontal length change and includes a spring loaded caliper 43. The third measuring device 44 is along the length altering strut and also includes a spring loaded caliper 45. Of course, other measuring methods can be used, but this method may be easily read periodically during the testing.

The dial indicators could be spring loaded so that the measuring lengths are always under some slight tension. Stainless steel single stranded wire is an appropriate measuring material. If a wall has a structural side and a non-structural side it is preferable to window the nonstructural side so that any benefit of the structural side may be determined.

Two examples are shown of a typical test, one showing a test which passed and another showing a test which failed. These are shown in the following tables with Table 1 showing measurements at 500 psi gauge pressure. Although the diagonal distance changed from 3.464 at 500 psi to 3.766 at 2,350 psi, neither the vertical nor the horizontal made any change.

In Table 2 a wall section is shown which did not pass and it can be seem that not only did the diagonal change but both the vertical and horizontal also changed. As above, these tests take into consideration the actual effect of wall covering and damage. Because of the infinite variations possible in the construction and level of workmanship within a building, the results from the tests of the present invention cannot be relied upon as an absolute guide to what each and every wall in a building will actually withstand. The tests do, however, provide an accurate and reliable indication of where weaknesses would likely occur within similarly placed walls in the complex. These tests also help to show areas of weakness and indicate where appropriate repair procedures can be designed and applied.

TABLE 1

| Gauge psi | Diag. | Vert. | Horiz. |
|---|---|---|---|
| 500 | 3.464" | 3.336" | 3.274" |
| 1,000 | 3.505" | 3.336" | 3.274" |
| 1,500 | 3.625" | 3.336" | 3.274" |
| 2.000 | 3.709" | 3.336" | 3.274" |
| 2,350 | 3.766" | 3.336" | 3.274" |
| 500 | 3.703" | 3.336" | 3.274" |

TABLE 2

| Guage psi | Diag. | Vert. | Horiz. |
|---|---|---|---|
| 500 | 3.321" | 3.226" | 3.334" |

TABLE 2-continued

| Guage psi | Diag. | Vert. | Horiz. |
|---|---|---|---|
| 1,000 | 3.424" | 3.257" | 3.334" |
| 1,500 | 3.535" | 3.270" | 3.401" |
| 2,000 | 3.649" | 3.288" | 3.445" |
| 2,250 | 3.710" | 3.288" | 3.471" |
| 2,500 | 3.771" | 3.306" | 3.500" |
| 500 | 3.658" | 3.306" | 3.500" |

Further detail of the attachment methods are best seen by viewing FIGS. 2 through 8. First of all, in FIG. 1 it can be seen that length altering strut 33 is placed outside of the wallboard pieces 23, 24 and 25. This is possible because the strut supporting portions are also positioned outside of the wallboard. Another feature of the present invention is the use of individual brackets 46 which may be placed in any pair of holes 47 which the structure permits. Thus, the positioning of electrical wires, studs and the like may be compensated for and the shoes solidly applied. The brackets 46 are secured by bolts 48 to the shoes through holes 47. They are then secured by lag screws 49 to the structural members. Of course, the attachment method depends upon the type of members present and if there are metal members, then, of course, welding or other attachment means can be used.

Figure 5:
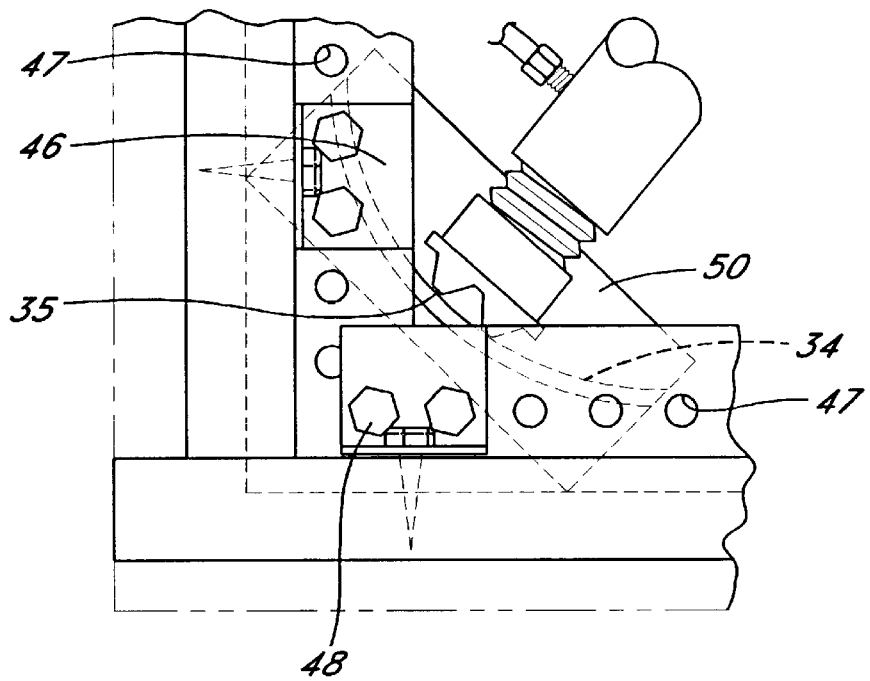
FIG. 5 is an enlarged view taken along line 5—5 of FIG. 4.
Figure 6:
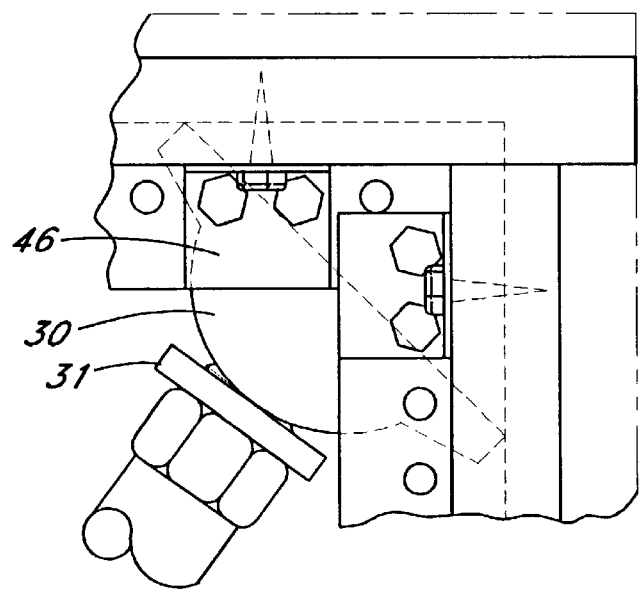
FIG. 6 is an enlarged view taken along line 6—6 of FIG. 4.
Figure 7:
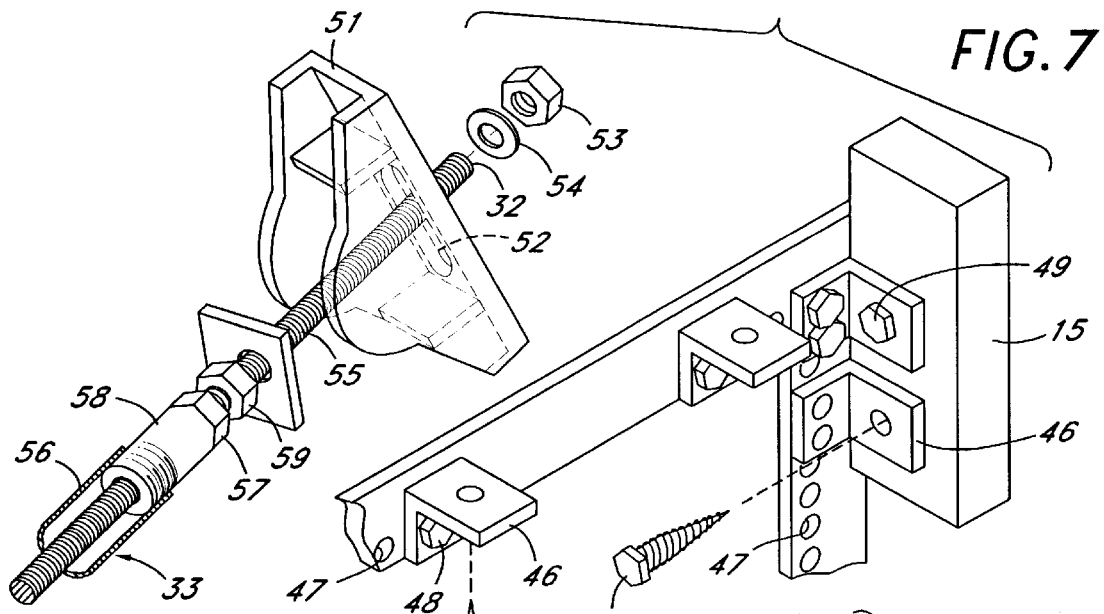
FIG. 7 is an exploded perspective view of the upper portion of the apparatus of FIG. 4 roughly along the area indicated by line 6—6.
Figure 8:
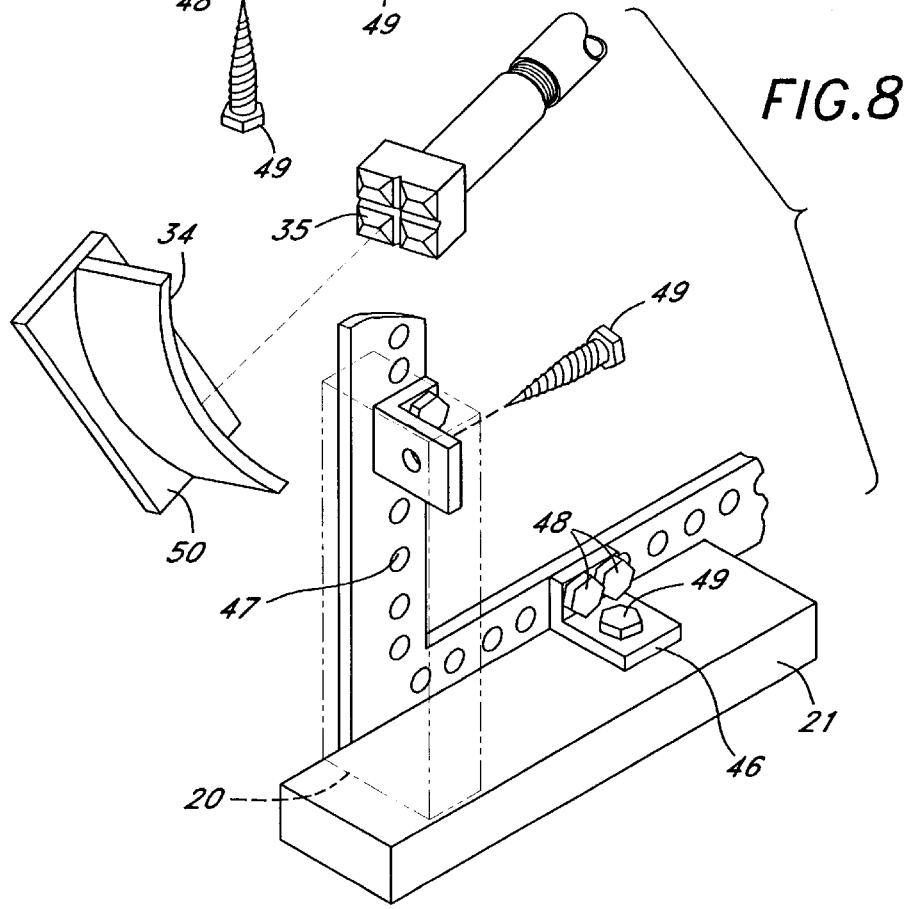
FIG. 8 is an exploded perspective view of the lower portion of the apparatus of FIG. 4 roughly taken along line 5—5 of FIG. 4.

As shown best in FIG. 5, the lower end 35 of strut 33 rests at a radius of the curved strut supporting portion 34 and a plate 50 helps hold it in-place. Along the upper end, plate 31 rests on a pair of curved strut supporting portions 30. These in turn are held by a central web 51 which includes a slot 52. This provides a method of holding the upper end 32 of strut 33 onto central web 51. A nut 53 and washer 54 may be inserted on the threaded portion 55 of strut assembly 33. This threaded portion can be used to alter the overall length since it passes within the central portion 56 of strut 33 and is secured in-place by nuts 57 welded to the short length of pipe 58 and nut 59. Thus, after the shoes have been affixed, an appropriate central portion 56 may be selected and threaded portion 55 may be inserted in an appropriate length into nut 57. Afterwards, threaded portion 55 is passed through slot 52 and loosely secured in-place by nut 53.

The lower end may then be set in-place and the overall length appropriately adjusted.

The testing method of the present invention has led to some interesting discoveries which are not used in typical engineering calculations. For instance, closely nailed plywood can greatly strengthen a wall and no benefit is given for such wall covering in the calculations. It is, of course, realized that dry rot and termites can substantially weaken a wall and this is impossible to determine by normal engineering calculations. The shear testing is analogous to the force of seismic activity or high winds since such forces typically provide a shearing force on a structure.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A method for the in-place testing of the shear strength of a rectangular area of a wall, said wall having vertical and horizontal structural elements, said rectangular area having an upper, first-side corner and a lower, second-side corner, an upper side, a first side and an second side, and a lower side, said method comprising the steps of:

affixing a first shoe to the upper, first-side corner, said first shoe having a first strut-supporting portion;

affixing a second shoe to the lower, second-side corner, said second shoe having a second strut-supporting portion;

placing a force applying length altering strut between the first and second strut-supporting portions said force applying length altering strut including means for applying a controlled length altering change;

altering the length of said force applying length-altering strut by changing the length of said means for applying a controlled length altering change; and measuring at least one dimension of said rectangular area after the length of the force applying length-altering strut has been altered.

2. The method of in-place testing of the shear strength of a rectangular area of a wall of claim 1 wherein the length of the force applying length altering strut is lengthened during said altering step.

3. The method of in-place testing of the shear strength of a rectangular area of a wall of claim 2 wherein said lengthening step is carried out by placing a hydraulic cylinder assembly in said length altering strut.

4. The method of in-place testing of the shear strength of a rectangular area of a wall of claim 3 wherein the pressure in said hydraulic cylinder is continuously measured.

5. The method of in-place testing of the shear strength of a rectangular area of a wall of claim 1 wherein said length altering strut has an upper affixing point and a lower affixing point, an upper end and a lower end and said length altering strut is movably affixed to said first strut supporting portion to assist in assembly.

6. The method of in-place testing of the shear strength of a rectangular area of a wall of claim 1 wherein said measuring step includes measuring along said length altering strut.

7. The method of in-place testing of the shear strength of a rectangular area of a wall of claim 6 wherein the measuring step further includes measuring along a side of said rectangular area, and a top or bottom.

8. A method for determining the strength of a wall of a completed structure, said wall having a plurality of vertical studs affixed to a sole at the bottom and to a plate at the top, the wall having an exterior surface covering and an interior surface covering and said wall having a rectangular area including the sole and the plate, a first vertical side and a second vertical side, said rectangular having an upper first side corner and a lower opposite corner said method comprising:

removing an area of one of said exterior or interior surface coverings at each of said corners to expose an upper vertical portion of a vertical member, said upper vertical portion at the upper corner being an exposed upper vertical portion and a plate portion of the plate at the upper corner, said plate portion being an exposed plate portion and a lower vertical portion of another vertical member at the lower opposite corner, said lower vertical portion being an exposed lower vertical portion and a sole portion of the sole at the lower opposite corner, said sole portion of the sole being an exposed sole portion;

affixing an upper shoe to the exposed plate and exposed upper vertical portion at the upper corner, said upper shoe having a contact portion positioned away from an outer plane of said removed surface covering;

affixing a lower shoe to the exposed sole and exposed lower vertical portion at the lower opposite corner, said lower shoe having a contact portion positioned away from an outer plane of said removed surface covering;

affixing a length altering strut between said contact portions of said upper and lower shoes;

altering the length of said length altering strut; and measuring the change in size of said rectangular area.

9. The method of in-place testing of the shear strength of a rectangular area of a wall of claim 8 wherein the length of said length altering strut is altered by a hydraulic cylinder assembly placed along said length altering strut.

10. The method of in-place testing of the shear strength of a rectangular area of a wall of claim 9 wherein the hydraulic cylinder assembly includes a pressure gauge and the measuring step is made at predetermined intervals of pressure.

11. The method of in-place testing of the shear strength of a rectangular area of a wall of claim 10 wherein said measuring step includes measuring the height, width and diagonal of said rectangular area.

12. An assembly for the in-place testing of an area of an existing wall having a pair of shoes for affixing to opposite corners of a wall area, said wall area including a plurality of studs, a lower sole and an upper plate, said pair of shoes including an upper shoe and a lower shoe and said pair of shoes and a length altering strut, said assembly comprising:

a lower shoe being in the shape of a right angle having a base and a vertical side, an inner surface and an outer surface, said base and said vertical side each having a plurality of holes therethrough and a plurality of right angled brackets also having holes therethrough whereby the lower shoe can be affixed to the sole and a vertical stud by affixing a plurality of right angled brackets to the inner surface of the vertical side and a stud and affixing a plurality of right angled brackets to the inner surface of the base and the sole, said lower shoe having a curved strut supporting plate affixed to the outer surface near the intersection of the base and the vertical side;

an upper shoe being in the shape of a right angle having a base and a vertical side, an inner surface and an outer surface, said base and said vertical side each having a plurality of holes therethrough and a plurality of right angled brackets also having holes therethrough whereby the upper shoe can be affixed to the plate and a vertical stud by affixing a plurality of right angled brackets to the inner surface of the vertical side and a stud and affixing a plurality of right angled brackets to the inner surface of the base and the plate, said upper shoe having a curved strut supporting plate affixed to the outer surface near the intersection of the base and the vertical side; and a length altering strut having a straight portion an upper end, a lower end, and a length altering piece along a portion of the straight portion thereof.

13. The assembly of claim 12 wherein said length altering piece is a hydraulic cylinder assembly.

14. The assembly of claim 12 wherein said upper shoe has a pair of curved strut supporting plates affixed to a central base and the central base has a slotted opening therein and the upper end of said length altering strut is threaded and has a flat member held thereon which rests on said curved strut supporting plates and a nut is held near the upper end to permit the length altering strut to be hangingly supported adjacent said slotted opening during assembly.

15. The assembly of claim 14 wherein the length of said length altering strut may further be adjusted by the threading in and out of a threaded stud at the upper end of said strut along a nut welded to a length of pipe about which a long member of the length altering strut is affixed.

* * * * *